US00PP26192P3

(12) United States Plant Patent
Zaiger et al.

(10) Patent No.: US PP26,192 P3
(45) Date of Patent: Dec. 8, 2015

(54) INTERSPECIFIC TREE NAMED 'AUTUMN TREAT'

(50) Latin Name: **Interspecific *Prunus* species**
Varietal Denomination: AUTUMN TREAT

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 98 days.

(21) Appl. No.: 13/999,782

(22) Filed: Mar. 21, 2014

(65) Prior Publication Data

US 2015/0271966 P1 Sep. 24, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular bearer of large size fruit.
2. Fruit with very good flavor and eating quality.
3. Fruit with attractive red skin color.
4. Fruit with good storage and shipping quality.
5. Fruit maturity very late in the maturity season.

1 Drawing Sheet

Botanical designation: Interspecific *Prunus* species.
Variety denomination: 'AUTUMN TREAT'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecifics, which are known to us, and mentioned herein, 'Flavor Grenade' Interspecific (U.S. Plant Pat. No. 12,097) and 'Flavorfall' Interspecific (U.S. Plant Pat. No. 11,990).

STATEMENT REGARDING FEDERALLY SPONSORED RESEARCH AND DEVELOPMENT

Not applicable.

ORIGIN OF THE VARIETY

The new and distinct variety of interspecific tree [(*Prunus salicina*×(*Prunus salicina*×*Prunus armeniaca*))] was originated by us as an open pollinated seedling from seed collected from 'Flavor Grenade' Interspecific (U.S. Plant Pat. No. 12,097). A large number of these open pollinated seedlings were grown on their own root and under close and careful observation, one such seedling exhibited desirable tree and fruit characteristics and was selected in 1998 for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific *Prunus* species tree (Plum×Plumcot), is of large size, vigorous, upright growth and a regular and productive bearer of large size, yellow flesh fruit with very good flavor and eating quality. The fruit is further characterized by having firm flesh, an attractive red skin color and by maturing very late in the season. In comparison to its seed parent 'Flavor Grenade' Interspecific (U.S. Plant Pat. No. 12,097) the fruit of the new variety is larger in size, completely overspread with red skin color and is approximately 84 days later in maturity. In comparison to the commercial variety 'Flavorfall' Interspecific (U.S. Plant Pat. No. 11,990) the fruit of the new variety is approximately 26 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 14 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 14 year old specimens grown near Modesto, Calif., with color in accordance with Munsell Book of Color published in 1958.

Tree:

*Size.*—Large, usually pruned to 3 to 3.5 meters in height and width for economical harvesting of fruit. Size varies with different cultural practices.

*Vigor.*—Semi-vigorous, tree growth of 1.5 to 1.5 meters the first growing season. Varies slightly with type of soil, fertility and climatic conditions.

*Form.*—Upright, usually pruned to vase shape to allow more sunlight to center of tree to enhance fruit color and health of fruit spurs.

*Branching habit.*—Upright, crotch angle approximately 30°, increases with heavy crop load.

*Productivity.*—Productive, fruit thinning necessary for desired market size fruit. Fruit set varies with climatic conditions during bloom season.

*Bearer.*—Regular, adequate fruit set 12 consecutive years. No alternate bearing observed.

*Fertility.*—Self-sterile, pollinator required.

*Density.*—Medium dense, controlled by pruning.

*Hardiness.*—Hardy in all stone fruit growing areas of California. Tree grown in USDA Hardiness Zone 9. Winter chilling requirement approximately 800 hours at or below 45° F.

Trunk:

*Size.*—Medium. Average circumference 68.4 cm at 26.9 cm above ground on a 14 year old tree.

*Stocky.*—Medium stocky.

*Texture.*—Medium shaggy, roughness increases with age of tree.

*Color.*—Varies from 10YR 4/2 to 10YR 2/2.

Branches:

*Size.*—Medium. Average circumference 15.6 cm at 1.2 meters above ground.

*Surface texture.*—New growth relatively smooth. Mature growth medium rough, roughness increases with age.

*Lenticels.*—Average number 33 in a 25.8 sq cm area. Size — medium to large. Average length 3.9 mm. Average width 1.3 mm. Color varies from 5YR 5/6 to 5YR 5/8.

*Color.*—New growth varies from 5GY 5/6 to 5YR 4/6. Mature growth varies from 5YR 3/6 to 7.5YR 3/4, varies with age of growth.

Leaves:

*Size.*—Medium to large. Average length 85.9 mm. Average width 42.4 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Size — medium. Average length 13.6 mm. Average width 1.4 mm. Longitudinally grooved. Surface glabrous. Color varies from 2.5GY 7/4 to 7.5R 4/6.

*Glands.*—Type — globose. Size — small. Average length 0.9 mm. Average diameter 0.5 mm. Number varies from 2 to 7, average number 5. Located primarily on upper portion of petiole and the base of the leaf blade. Color 2.5GY 5/6 to 7.5R 3/4.

*Stipules.*—None present.

*Color.*—Upper surface varies from 2.5GY 4/4 to 2.5GY 3/4. Lower surface varies from 2.5GY 4/4 to 5GY 4/4. Midvein color varies from 2.5GY 8/2 to 2.5GY 2 8/6.

Flower buds:

*Size.*—Small to medium. Average length 9.8 mm. Average diameter 5.5 mm.

*Hardiness.*—Hardy with respect to California winters.

*Form.*—Plump, conical, becoming elongated as it matures.

*Pedicel.*—Size — small to medium. Average length 12.4 mm. Average width 0.5 mm. Color varies from 2.5GY 7/6 to 2.5GY 7/8. Surface — glabrous.

*Color.*—N 9.5/(white).

*Number of buds per spur.*—Varies from 3 to 15, average number 7. Varies with age of spur.

Flowers:

*Blooming period.*—Date of First Bloom Feb. 24, 2013. Date of Petal Fall Mar. 6, 2013, varies slightly with climatic conditions.

*Size.*—Medium. Average height 11.8 mm. Average diameter 19.6 mm.

*Petals.*—Normally 5, alternately arranged to sepals. Size — small to medium. Average length 9.5 mm. Average width 7.9 mm. Form — elliptical. Margin — sinuate. Both upper and lower surfaces glabrous. Color — N 9.5/(white). Arrangement — free.

*Sepals.*—Normally 5, alternately arranged to petals. Size — small. Average length 2.8 mm. Average width 2.0 mm. Shape — triangular, apex rounded. Margin — entire. Both upper and lower surfaces glabrous. Color — upper surface varies from 5GY 6/6 to 5GY 5/6. Lower surface varies from 2.5GY 6/6 to 2.5GY 5/6. Upper edges of some sepals 2.5R 3/10.

*Stamens.*—Average number per flower 33. Average length 8.9 mm. Filament color N 9.5/(white). Anther color varies from 10R 5/10 to 5YR 6/10.

*Pollen.*—Present, self-sterile, pollinator required. Color varies from 2.5Y 8/10 to 2.5Y 7/12.

*Pistil.*—Number — normally one. Surface — glabrous. Average length 9.0 mm. Position of stigma an average of 0.7 mm below anthers. Color varies from 10Y 8.5/6 to 10Y 9/6.

*Fragrance.*—Wanting.

*Color.*—N 9.5/(white).

*Pedicel.*—Average length 13.5 mm. Average width 0.5 mm. Surface — glabrous. Color varies from 2.5GY 7/8 to 2.5GY 7/10.

*Number flowers per flower bud.*—Average 2, varies from 1 to 3.

Fruit:

*Maturity when described.*—Firm ripe.

*Date of first picking.*—Oct. 31, 2013.

*Date of last picking.*—Nov. 8, 2013, varies slightly with climatic conditions.

*Size.*—Large. Average diameter axially 68.6 mm. Average transversely in suture plane 61.3 mm. Average weight 170.4 grams, varies slightly with fertility of the soil, amount of thinning and climatic conditions.

*Form.*—Slightly elongated.

*Suture.*—Nearly smooth, extends from base to apex.

*Ventral surface.*—Very slightly lipped.

*Apex.*—Rounded.

*Base.*—Flat to slightly retuse.

*Stem cavity.*—Rounded. Average depth 3.8 mm. Average diameter 7.6 mm.

Stem:

*Size.*—Large. Average length 20.8 mm. Average diameter 2.0 mm.

*Color.*—Varies from 5YR 3/6 to 7.5YR 3/8.

Skin:

*Thickness.*—Medium.

*Surface.*—Slightly waffled.

*Bloom.*—Moderate amount.

*Tendency to crack.*—None.

*Color.*—Ground color varies from 5Y 9/4 to 7.5Y 9/4. Overspread with 7.5R 2/4 to 7.5R 2/6.

*Tenacity.*—Tenacious to flesh.

*Astringency.*—Undetected.

Flesh:

*Ripens.*—Evenly.

*Texture.*—Firm, meaty.

*Fibers.*—Few, small, tender.

*Firmness.*—Firm, comparable to other commercial interspecific varieties.

*Aroma.*—Moderate aroma.

*Amydgalin.*—Undetected.

*Eating quality.*—Very good.

*Flavor.*—Very good, a good balance between acid and sugar.

*Juice.*—Moderate amount, enhances flavor.

*Brix.*—Average Brix 18.6°, varies slightly with amount of fruit per tree and climatic conditions.

*Color.*—Varies from 2.5Y 7/6 to 5Y 7/6.

*Pit cavity.*—Average length 28.9 mm. Average width 18.4 mm. Average depth 9.1 mm. Color varies from 10YR 5/6 to 7.5YR 5/6.

Stone:

*Type.*—Clingstone.

*Size.*—Medium. Average length 26.9 mm. Average width 17.6 mm. Average thickness 9.4 mm.

*Form.*—Obovoid.

*Base.*—Flat.

*Apex.*—Pointed. Average length 0.6 mm.

*Surface.*—Slightly pitted throughout.

*Sides.*—Unequal, one side extending further from suture plane.

*Ridges.*—Small narrow ridge on each side of suture extending from base to apex.

*Tendency to split.*—None.

*Color.*—Varies from 7.5YR 6/6 to 7.5YR 5/6 when dry.

Kernel:

*Size.*—Small to medium. Average length 15.5 mm. Average width 8.0 mm. Average depth 4.9 mm.

*Form.*—Ovoid.

*Viability.*—Viable, complete embryo development.

*Skin color.*—Varies from 7.5YR 5/6 to 7.5YR 4/6.

Use: Dessert.

*Market.*—local and long distance.

Keeping quality: Good, held firm in cold storage 3 weeks at 38° to 42° F. without shriveling, internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

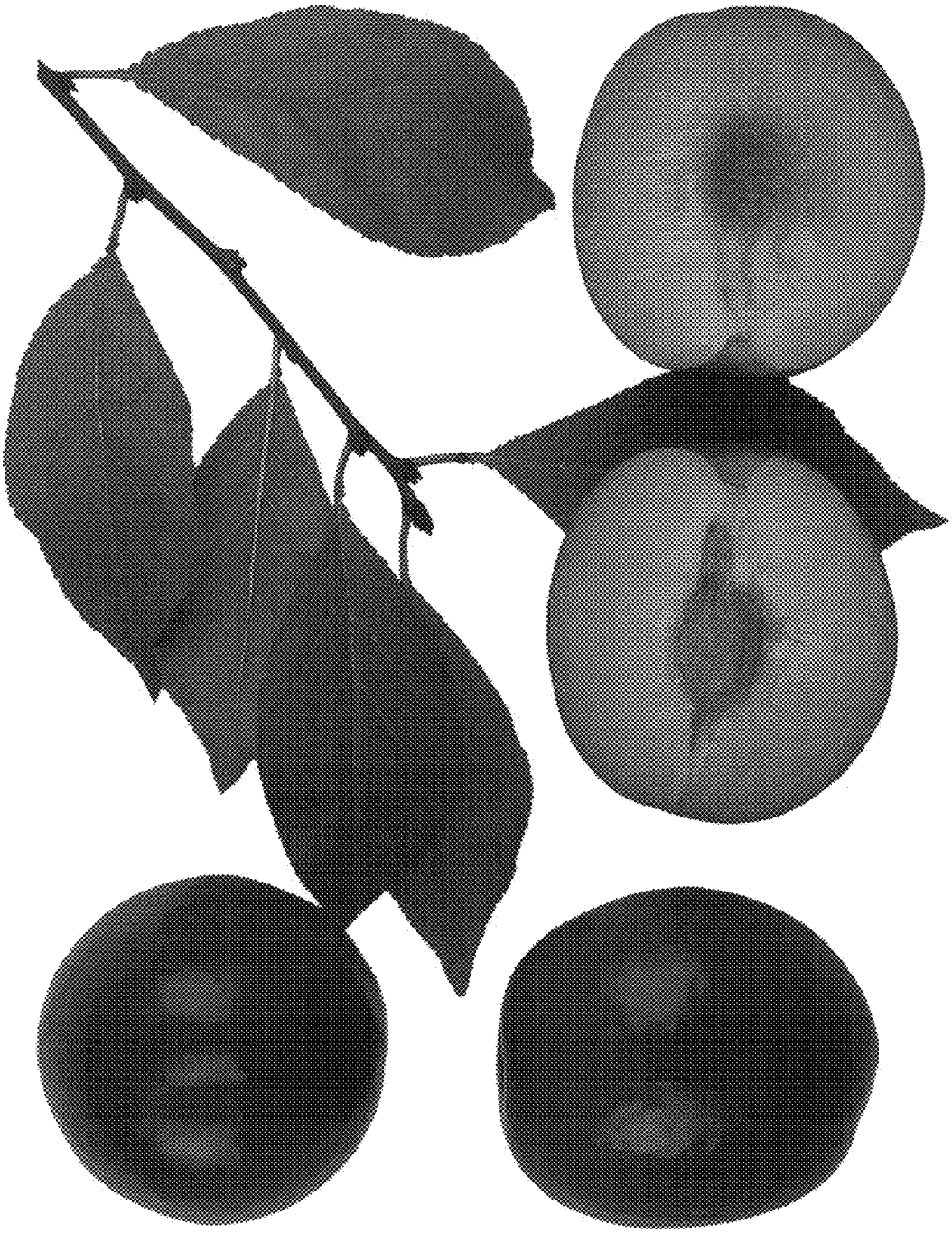

* * * * *